United States Patent [19]

Guillaume et al.

[11] 4,324,790
[45] Apr. 13, 1982

[54] ANTIPSYCHOTIC TETRAHYDROPYRIDINYL-INDOLES, COMPOSITIONS AND METHOD OF USE

[75] Inventors: Jacques Guillaume, Sevran; Lucien Nedelec, Le Raincy; Claude Dumont, Nogent-sur-Marne, all of France

[73] Assignee: Roussel Uclaf, Paris, France

[21] Appl. No.: 163,966

[22] Filed: Jun. 30, 1980

[30] Foreign Application Priority Data

Jul. 13, 1979 [FR] France ................... 79 18217

[51] Int. Cl.³ ................... A61K 31/44; C07D 401/04
[52] U.S. Cl. ................... 424/263; 546/273
[58] Field of Search ................... 546/273; 424/263

[56] References Cited

U.S. PATENT DOCUMENTS

| | | | |
|---|---|---|---|
| 3,850,938 | 11/1974 | Derible et al. | 546/273 |
| 3,980,658 | 9/1976 | Possanza et al. | 546/273 |
| 3,993,764 | 11/1976 | Dumont et al. | 424/267 |
| 4,196,209 | 4/1980 | Dumont et al. | 546/273 |
| 4,232,031 | 11/1980 | Dumont et al. | 546/273 |

FOREIGN PATENT DOCUMENTS 2227873 11/1974 France .

OTHER PUBLICATIONS

Freter, J. Org. Chem., 1975, vol. 40 (7), pp. 2525–2529.

Primary Examiner—Henry R. Jiles
Assistant Examiner—Natalia Harkaway
Attorney, Agent, or Firm—Hammond & Littell, Weissenberger and Muserlian

[57] ABSTRACT

Novel tetranydro-pyridinyl-indoles of the formula

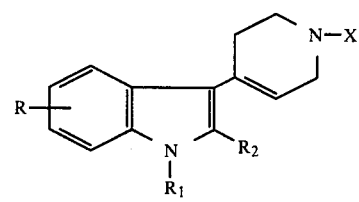

wherein X is selected from the group consisting of alkyl of 1 to 6 carbon atoms, alkenyl of 2 to 5 carbon atoms, alkynyl of 3 to 5 carbon atoms, cycloalkyl of 5 to 6 carbon atoms, cycloalkylalkyl of 4 to 7 carbon atoms, aralkyl of 7 to 12 carbon atoms, hydroxyalkyl of 2 to 5 carbon atoms and phenoxyalkyl of 1 to 5 alkyl carbon atoms, R is selected from the group consisting of hydrogen, halogen, alkoxy of 1 to 3 carbon atoms, nitro, amino, trifluoromethyl and methylthio, $R_1$ and $R_2$ are individually selected from the group consisting of hydrogen and alkyl of 1 to 3 carbon atoms with the proviso that if R is hydrogen, halogen or alkoxy of 1 to 3 carbon atoms, X must be hydroxyalkyl or phenoxyalkyl and their non-toxic, pharmaceutically acceptable acid addition salts having neuroleptic, antipsychotic and antiemetic activity and their preparation.

15 Claims, No Drawings

ANTIPSYCHOTIC TETRAHYDROPYRIDINYL-INDOLES, COMPOSITIONS AND METHOD OF USE

STATE OF THE ART

Literature relating to indole derivatives include French Pat. No. 2,227,873, U.S. Pat. Nos. 4,195,081, 4,196,209 and 3,993,764, copending, commonly assigned U.S. patent application Ser. No. 2,453 filed Jan. 10, 1979 and J. Org. Chem., Vol. 40 (1975) No. 17. p. 2527.

OBJECTS OF THE INVENTION

It is an object of the invention to provide the novel indoles of formula I and their non-toxic, pharmaceutically acceptable acid addition salts and a process for their preparation.

It is a further object of the invention to provide novel neuroleptic, antiemetic and antipsychotic compositions and to provide novel method of treating vomitting and psychic problems in warm-blooded animals.

These and other objects and advantages of the invention will become obvious from the following detailed description.

THE INVENTION

The novel compounds of the invention are selected from the group consisting of an indole of the formula

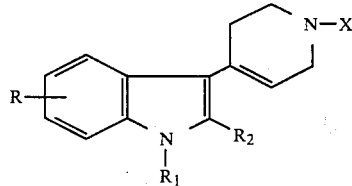

I wherein X is selected from the group consisting of alkyl of 1 to 6 carbon atoms, alkenyl of 2 to 5 carbon atoms, alkynyl of 3 to 5 carbon atoms, cycloalkyl of 5 to 6 carbon atoms, cycloalkylalkyl of 4 to 7 carbon atoms, aralkyl of 7 to 12 carbon atoms, hydroxyalkyl of 2 to 5 carbon atoms and phenoxyalkyl of 1 to 5 alkyl carbon atoms, R is selected from the group consisting of hydrogen, halogen, alkoxy of 1 to 3 carbon atoms, nitro, amino, trifluoromethyl and methylthio, $R_1$ and $R_2$ are individually selected from the group consisting of hydrogen and alkyl of 1 to 3 carbon atoms with the proviso that if R is hydrogen, halogen or alkoxy of 1 to 3 carbon atoms, X must be hydroxyalkyl or phenoxyalkyl and their non-toxic, pharmaceutically acceptable acid addition salts. The group R may be in any position on the indole but is preferably in the 5- or 6-position, most preferably in the 5-position.

Examples of the substituents of formula I are alkyl of 1 to 6 or 1 to 3 carbon atoms such as methyl, ethyl, propyl, isopropyl, butyl, isobutyl, pentyl, or isopentyl; cycloalkyl of 5 to 6 carbon atoms, namely cyclopentyl and cyclohexyl; cycloalkylalkyl of 4 to 7 carbon atoms such as cyclopropylmethyl; alkenyl of 2 to 5 carbon atoms such as vinyl, allyl, buten-2-yl and penten-2-yl; alkynyl of 3 to 5 carbon atoms such as propargyl; aralkyl such as benzyl or phenethyl; hydroxyalkyl of 2 to 5 carbon atoms such as hydroxyethyl, hydroxypropyl, hydroxybutyl or hydroxypentyl; phenoxyalkyl of 1 to 5 alkyl carbon atoms such as phenoxymethyl; phenoxyethyl, phenoxypropyl, phenoxybutyl or phenoxypentyl; halogens suc; as fluorine, chlorine or bromine; and alkoxy of 1 to 3 carbon atoms such as methoxy, ethoxy or propoxy.

Examples of suitable acids for the non-toxic, pharmaceutically acceptable acid addition salts are inorganic acids such as hydrochloric acid, hydrobromic acid, nitric acid, sulfuric acid and phosphoric acid and organic acids such as formic acid, acetic acid, propionic acid, benzoic acid, maleic acid, fumaric acid, succinic acid, tartaric acid, citric acid, oxalic acid, glyoxylic acid, aspartic acid, alkanesulfonic acids such as methanesulfonic acid and ethanesulfonic acid, arylsulfonic acids such as benzenesulfonic acid and p-toluene sulfonic acid and arylcarboxylic acids.

Among the preferred compounds of formula I are those wherein X is hydroxyalkyl of 2 to 5 carbon atoms, those wherein X is phenoxyalkyl of 1 to 5 alkyl carbon atoms, those wherein X is alkyl of 1 to 6 carbon atoms, cycloalkyl of 5 to 6 carbon atoms, cycloalkylalkyl of 4 to 7 carbon atoms, alkenyl of 2 to 5 carbon atoms, alkynyl of 3 to 5 carbon atoms or aralkyl of 7 to 12 carbon atoms when R is —NO$_2$, —NH$_2$, —CF$_3$ or CH$_3$S— and their non-toxic, pharmaceutically acceptable acid addition salts. A particularly preferred compound is 3-(1-propyl-1,2,3,6-tetrahydro-4-pyridinyl)-5-nitro-1H-indole hydrochloride.

The novel process of the invention for the preparation of a compound of formula I wherein X is hydroxyalkyl of 2 to 5 carbon atoms comprises reacting a compound of the formula

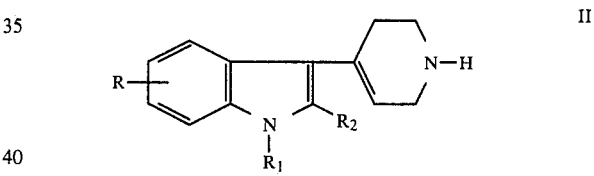

II wherein R, $R_1$ and $R_2$ have the above definitions with a compound of the formula

Hal—X'    III when Hal is chlorine, bromine or iodine and X' is tetrahydropyranyloxyalkyl of the formula

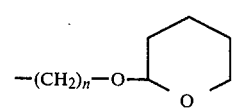

—(CH$_2$)$_n$—O— wherein n is 2,3,4 or 5 to obtain a compound of the formula

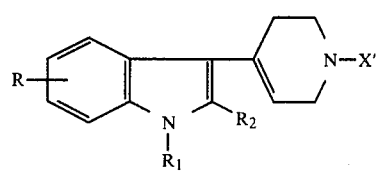

IV and hydrolyzing the latter to obtain a compound of formula I wherein X is hydroxyalkyl of 2 to 5 carbon atoms and optionally reacting the latter with an acid to form the acid addition salt thereof.

Preferably, the reaction of the compounds of formulae II and III is effected in an organic solvent such as isobutyl methyl ketone in the presence of sodium carbonate and the hydrolysis of the compound of formula IV is effected with hydrochloric acid in an alkanol such as methanol or ethanol.

The novel process of the invention for the preparation of compounds of formula I wherein X is other than hydroxyalkyl of 2 to 5 carbon atoms comprises reacting a compound of formula II with a compound of the formula Hal—X''  III'' wherein Hal has the above definition and X'' is one of the substituents of X other than hydroxyalkyl of 2 to 5 carbon atoms to obtain the corresponding compound of formula I which is optionally reacted with an acid to form the corresponding acid addition salt.

Preferably, the reaction of the compounds of formulae II and III' is effected in an organic solvent such as dimethylformamide in the presence of sodium carbonate but it may also be effected in isobutyl methyl ketone in the presence of silver oxide, sodium carbonate or triethylamine.

The acid addition salts of formula I are prepared in the classical manner by reacting substantially stoichiometric amounts of the acid and the free base of formula I.

The novel therapeutic compositions of the invention are comprised of a neuroleptically, antipsychotically and antiemetically effective amount of at least one compound of formula I and its non-toxic, pharmaceutically acceptable acid addition salts and an inert pharmaceutical carrier. The compositions may be in the form of tablets, dragees, gelules, granules, suppositories and injectable solutions or suspensions.

Examples of suitable excipients or pharmaceutical carriers are talc, arabic gum, lactose, starch, magnesium stearate, cacao butter, aqueous and non-aqueous vehicles, fatty bodies of animal or vegetable origin, paraffinic derivatives, glycols, diverse wetting agents, dispersants or emulsifiers and preservatives.

Among the preferred compositions of the invention are those wherein X is hydroxyalkyl of 2 to 5 carbon atoms, those wherein X is phenoxyalkyl of 1 to 5 alkyl carbon atoms, those wherein X is alkyl of 1 to 6 carbon atoms, cycloalkyl of 5 to 6 carbon atoms, cycloalkylalkyl of 4 to 7 carbon atoms, alkenyl of 2 to 5 carbon atoms, alkynyl of 3 to 5 carbon atoms and aralkyl of 7 to 12 carbon atoms when R is $-NO_2$, $-NH_2$, $-CF_3$ or $CH_3S-$ and their non-toxic, pharmaceutically acceptable acid addition salts. A particularly preferred compound is 3-(1-propyl-1,2,3,6-tetrahydro-4-pyridinyl)-5-nitro-1H-indole hydrochloride.

The compositions are useful for the treatment of psychic troubles, of behavior troubles and character troubles as well as for the treatment of vomitting and nausea of all types.

The novel method of the invention for inducing neuroleptic, antiemetic and antipsychotic activity in warm-blooded animals, including humans, comprises administering to warm-blooded animals a sufficient amount of at least one compound of formula I and its non-toxic, pharmaceutically acceptable acid addition salts to induce antiemetic, anti-psychotic and neuroleptic activity. The compounds may be administered orally, rectally or parenterally. The usual daily dose is depending on the compound, the method of administration, the person treated and the complaint concerned. It can be, for example, from 0.1 to 4 mg/Kg per day by oral route in man.

The compounds of formula II which are not known may be prepared by reacting a compound of the formula

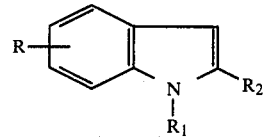

wherein R, $R_1$ and $R_2$ have the above definitions with 4-piperidone hydrochloride, preferably in an alkaline media but if $R_2$ is alkyl, preferably in an acid media. The reaction is preferably effected in 2 N methanolic potassium hydroxide solution.

The compounds of formula V wherein R is methylthio are prepared by reacting cuprous mercaptate with an indole of the formula

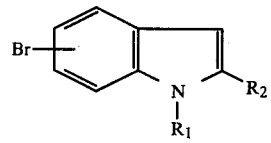

In the following examples there are described several preferred embodiments to illustrate the invention. However, it should be understood that the invention is not intended to be limited to the specific embodiments.

EXAMPLE 1

5-methylthio-3-(1-propyl-1,2,3,6-tetrahydro-4-pyridinyl)-1H-indole hydrochloride

STEP A: 5-methylthio-1H-indole

A mixture of 22.7 g 5-bromo-1H-indole of 230 ml of quinoline, 16 g of cuprous methyl mercaptate [prepared by Engelhardt, J. Med. Chem. II (1968), p. 329] and 34 ml of anhydrous pyridine was refluxed with stirring for 5 hours and was then cooled and added to a mixture of 1 liter of 2 N hydrochloric acid and 1 liter of ethyl acetate. The mixture was filtered and the decanted organic phase was washed with 2 N hydrochloric acid and then with aqueous sodium chloride solution, dried and evaporated to dryness at 40° C. under reduced pressure. The 17.8 g of residue were chromatographed over silica gel and eluted with a 1-1 cyclohexane-benzene mixture to obtain 11.75 g of 5-methylthio-1H-indole.

U.V. Spectrum (ethanol):

| | | |
|---|---|---|
| Max. at 225 nm | $E_1^1 = 1812$ | $\epsilon = 29,400$ |
| Inflex. towards 250 nm | $E_1^1 = 710$ | |
| Inflex. towards 278 nm | $E_1^1 = 249$ | |
| Inflex. towards 294 nm | $E_1^1 = 188$ | |
| Inflex. towards 310 nm | $E_1^1 = 98$ | |

STEP B:
3-(1,2,3,6-tetrahydro-4-pyridinyl)-5-methylthio-1H-indole

A mixture of 22.1 g of the hydrate of 4-piperidone hydrochloride and 108 ml of 2 N methanolic potassium hydroxide solution was refluxed with stirring under an inert atmosphere for 16 hours and was cooled and poured into one liter of ice water. The mixture was stirred for 15 minutes and was filtered and the recovered product was washed with water, dried and crystallized from a 10-3 ethyl acetate-methanol mixture to obtain 14.8 g of 3-(1,2,3,6-tetrahydro-4-pyridinyl)-5-methylthio-1H-indole in the form of yellow crystals melting at 210° C.

STEP C:
3-(1-propyl-1,2,3,6-tetrahydro-4-pyridinyl)-5-methylthio-1H-indole hydrochloride A suspension of 7 g of the product of Step B, 6 g of sodium carbonate, 4.2 ml of propyl iodide and 160 ml of dimethylformamide was stirred at room temperature for 4 hours and was then poured into water. The mixture was filtered and the product was washed and dried to obtain 7.1 g of a yellow crystalline solid which was crystallized from isopropanol to obtain 6 g of 3-(1-propyl-1,2,3,6-tetrahydro-4-pyridinyl)-5-methylthio-1H-indole in the form of yellow crystals melting at 176° C.

A suspension of 5 g of the said product in 300 ml of ethyl acetate cooled to 0° to 5° C. was admixed with an ethyl acetate solution saturated with gaseous hydrogen chloride and the mixture was filtered. The recovered product was washed with ethyl acetate, dried and crystallized for a mixture of 500 ml of isopropanol and 100 ml of methanol to obtain 5.2 g of 3-(1-propyl-1,2,3,6-tetrahydro-4-pyridinyl)-5-methylthio-1H-indole hydrochloride in the form of yellow crystals melting at 236° C.

Analysis: $C_{17}H_{22}N_2S.HCl$; molecular weight=322.9
Calculated: %C 63.24; %H 7.18; %N 8.67; %S 9.93; %Cl 10.98; Found: %C 63.4; %H 7.2; %N 8.5; %S 9.9; %Cl 11.1.

EXAMPLE 2
3-(1-propyl-1,2,3,6-tetrahydro-4-pyridinyl)-5-nitro-1H-indole hydrochloride

STEP A:
3-(1,2,3,6-tetrahydro-4-pyridinyl)-5-nitro-1H-indole hydrochloride A mixture of 7.7 g of 5-nitro-1H-indole and 225 ml of ethanol saturated with hydrogen chloride and 22.5 g of the hydrate of 4-piperidone hydrochloride was refluxed for 3 hours under a nitrogen atmosphere and the mixture was then stirred at room temperature for one hour and at 0° C. for another hour. The mixture was filtered and the recovered product was rinsed with iced ethanol, with ethyl acetate and ether to obtain 14 g of raw product. The latter was crystallized from 600 ml of 1-1 methanol-water mixture and after standing overnight at 0° to 5° C., the mixture was filtered. The product was rinsed with methanol and dried to obtain 9.8 g of 3-(1,2,3,6-tetrahydro-4-pyridinyl)-5-nitro-1H-indole hydrochloride melting at 275° C.

Analysis: $C_{13}H_{14}N_3ClO_2$; molecular weight=279.733
Calculated: %C 55.82; %H 5.04; %Cl 12.68; %N 15.02; Found: %C 56.0; %H 5.1; %Cl 12.8; %N 14.7.

STEP B:
3-(1-propyl-1,2,3,6-tetrahydro-4-pyridinyl)-5-nitro-1H-indole hydrochloride A mixture of 11.2 g of the product of Step A, 140 ml of dimethylformamide, 12.72 g of sodium carbonate and 6.4 ml of propyl iodide was stirred at room temperature under an inert atmosphere for 5½ hours and was then diluted with 300 ml of distilled water. After crystallization, the mixture was stirred for one hour and was vacuum filtered. The recovered product was rinsed with water, then with 25 ml of 50% aqueous ethanol and dried to obtain 11.5 g of crystals melting at 164° C. The product was chromatographed over silica gel and was eluted with an 8-2 chloroform-acetone mixture to obtain 9.5 g of crystalline 3-(1-propyl-1,2,3,6-tetrahydro-4-pyridinyl)-5-nitro-1H-indole melting at 172° C.

6.13 g of the said product suspended in 150 ml of ethanol was iced and then an ethanolic solution of hydrogen chloride was added thereto with stirring to obtain a pH of 1. The mixture was stirred for 45 minutes under an inert atmosphere and was vacuum filtered. The product was rinsed with ethanol and dried to obtain 6.90 g of product which was crystallized from ethanol containing 20% water to obtain 5.85 g of 3-(1-propyl-1,2,3,6-tetrahydro-4-pyridinyl)-5-nitro-1H-indole hydrochloride melting at 240°-242° C.

Analysis: $C_{16}H_{19}O_2N_3.HCl$; molecular weight=321.814
Calculated: %C 59.71; %H 6.26; %Cl 11.01; %N 13.05; Found: %C 59.6; %H 6.2; %Cl 11.1; %N 12.9.

EXAMPLE 3
3-(1-propyl-1,2,3,6-tetrahydro-4-pyridinyl)-5-amino-1H-indole hydrochloride Using the procedure of Step C of Example 1, 5-amino-1H-indole was reacted to obtain 3-(1-propyl-1,2,3,6-tetrahydro-4-pyridinyl)-5-amino-1H-indole hydrochloride melting at 265° C.

Analysis: $C_{12}H_{22}N_3Cl$: molecular weight=291.891
Calculated: %C 65.85; %H 7.59; %N 14.39; %Cl 12.15; Found: %C 65.9; %H 7.7; %N 14.1; %Cl 12.1.

EXAMPLE 4
3-[1-(2-phenoxyethyl)-1,2,3,6-tetrahydro-4-pyridinyl]-5-chloro-1H-indole hydrochloride A mixture of 8 g of 3-[1,2,3,6-tetrahydro-4-pyridinyl]-5-chloro-1H-indole [described in French Pat. No. 2,362,628], 80 ml of dimethylformamide, 7.5 g of potassium carbonate and 9 g of β-bromo-phenethanol was stirred at 50° C. under an inert atmosphere for 2 hours and was then cooled to room temperature and was slowly diluted with 400 ml of distilled water. The mixture was stirred for 30 minutes and was vacuum filtered. The recovered product was washed with water, then with a 1-1 water-ethanol mixture and dried to obtain 14 g of raw product. 15.8 g of the said product were chromatographed over silica gel and eluted with a 6-3-1 chloroform-acetone-triethylamine mixture. The product was crystallized from ethanol to obtain 11.53 g of 3-[1-(2-phenoxyethyl)-1,2,3,6-tetrahydro-4-pyridinyl]-5-chloro-1H-indole melting at 172° C.

A suspension of the said product in 500 ml of ethanol was admixed by dropwise addition with ethanolic hydrogen chloride solution until the pH was acidic and the product was distilled by heating. The mixture was filtered and concentrated to half its volume. Crystallization was effected and the mixture was vacuum filtered. The mixture was washed with ethanol and dried to obtain 12.1 g of product melting at 190° C. which was crystallized from ethanol to obtain 9.25 g of 3-[1-(2-phenoxyethyl)-1,2,3,6-tetrahydro-4-pyridinyl]-5-chloro-1H-indole hydrochloride melting at 180° C., then 220° C.

Analysis: $C_{21}H_{22}Cl_2N_2O$; molecular weight = 389.3

Calculated: %C 64.78; %H 5.70; %N 7.20; Found: %C 64.1; %H 6.0; %N 6.9.

EXAMPLE 5

Neutral oxalate of 4-(1H-indol-3-yl)-3,6-dihydro-1-(2H)-pyridine-ethanol

STEP A:
3-[1-(2-{2-tetrahydropyranyloxy}-ethyl)-1,2,3,6-tetrahydro-4-pyridinyl]-1H-indole A solution of 6.93 g of 3-(1,2,3,6-tetrahydro-4-pyridinyl)-1H-indole [described in French Pat. No. 2,362,628] dissolved at 100° C. in 70 ml of isobutyl methyl ketone admixed with 11.13 g of sodium carbonate and 14 ml of 2-(2-chloroethoxy)-tetrahydro-2H-pyran was refluxed with stirring under an inert atmosphere for 5½ hours and was then cooled and poured into ice water. The mixture was extracted with ethyl acetate and the organic phase was washed with water, with aqueous sodium chloride solution, dried and evaporated to dryness. The 9.9 g of crystalline residue was chromatographed over silica gel and eluted with an 85-10-5 chloroform-acetonetriethylamine mixture to obtain 7.85 g of 3-[1-(2-{2-tetrahydropyranyloxy}-ethyl)-1,2,3,6-tetrahydro-4-pyridinyl]-1H-indole in the form of crystals melting at 135° C.

STEP B: Neutral oxalate of 4-(1H-indol-3-yl)-3,6-dihydro-1-(2H)-pyridine ethanol 15.6 ml of 6 N hydrochloric acid were added to a mixture of the product of Step A and 156 ml of 95% ethanol and the mixture was stirred for 3½ hours under an inert atmosphere and was then poured into one liter of water. 10 ml of sodium hydroxide were added to the mixture which was then filtered. The recovered crystals were washed with water and dried under reduced pressure to obtain 4.068 g of 4-(1H-indol-3-yl)-3,6-dihydro-1-(2H)-pyridine-ethanol melting at 164°-165° C.

3.815 g of the said product were dissolved in 200 ml of ethanol and 992 mg of oxalic acid were added to the solution. The formed crystals were redissolved in 1.5 liters of refluxing ethanol and the solution was filtered hot. The filtrate was concentrated and crystallization slowly occured. The mixture was vacuum filtered and the crystals were rinsed with ethanol to obtain 3.245 g of neutral oxalate of 4-(1H-indol-3-yl)-3,6-dihydro-1-(2H)-pyridine ethanol melting at 197°-200° C.

Analysis: $C_{32}H_{38}N_4O_6$; molecular weight = 574.683

Calculated: %C 66.88; %H 6.66; %N 9.74; Found: %C 66.6; %H 6.6; %N 9.6.

EXAMPLE 6

3-(1-cyclopropylmethyl-1,2,3,6-tetrahydro-4-pyridinyl)-5-nitro-1H-indole hydrochloride A mixture of 11.88 g of 3-(1,2,3,6-tetrahydro-4-pyridinyl)-5-nitro-1H-indole hydrochloride, 148 ml of dimethylformamide, 12.72 g of sodium carbonate and 4.8 ml of chloromethylcyclopropane was stirred at 70° C. under an inert atmosphere for 23 hours and the mixture was cooled. 450 ml of distilled water were added to the mixture which was then stirred for one hour and was vacuum filtered. The recovered product was rinsed with water and dried to obtain 10.8 g of raw product. The latter was chromatographed over silica gel and was eluted with a 6-3-1 chloroform-acetone-triethylamine mixture to obtain 8.3 g of 3-(1-cyclopropylmethyl-1,2,3,6-tetrahydro-4-pyridinyl)-5-nitro-1H-indole melting at 187°-188° C.

8.7 g of the said product were suspended in 130 ml of iced ethanol and ethanolic hydrogen chloride was added thereto with stirring until the pH was 1. The mixture was stirred under an inert atmosphere for 2 hours and was vacuum filtered. The product was rinsed with ethanol and dried to obtain 9.55 g of product which was crystallized from methanol to obtain 7.2 g of 3-(1-cyclopropylmethyl-1,2,3,6-tetrahydro-4-pyridinyl)-5-nitro-1H-indole hydrochloride in the form of crystals melting at 253°-255° C.

Analysis: $C_{17}H_{20}ClN_3O_2$; molecular weight = 333.826

Calculated: %C 61.16; %H 6.03; %Cl 10.62; %N 12.58; Found: %C 61.5; %H 6.1; %Cl 10.9; %N 12.4.

EXAMPLE 7

Neutral oxalate of 4-(5-chloro-1H-indol-3-yl)-1,2,3,6-tetrahydro-1-(2H)-pyridin propanol

STEP A:
3-[1-(3-{2-tetrahydropyranyloxy}-propyl)-1,2,3,6-tetrahydro-4-pyridinyl]-1H-indole A mixture of 11.6 g of 3-(1,2,3,6-tetrahydro-4-pyridinyl)-5-chloro-1H-indole, 120 ml of isobutyl methyl ketone, 15.9 g of sodium carbonate and 22 ml of 3-(3-chloropropyloxy)-tetrahydro-2H-pyran was stirred at 100°-105° C. under an inert atmosphere for 24 hours and was cooled and poured into 500 ml of water. The mixture was stirred for one hour and was extracted with ethyl acetate. The organic phase was washed with water and with aqueous sodium chloride solution, dried and evaporated to dryness. The 29.6 g of crystalline residue were chromatographed over silica gel and eluted with a 6-3-1 chloroform-acetone-triethylamine mixture to obtain 13.1 g of 3-[1-(3-{2-tetrahydropyranyloxy}-propyl)-1,2,3,6-tetrahydro-4-pyridinyl]-1H-indole in the form of crystals melting at 161° C.

STEP B: Neutral oxalate of 4-(5-chloro-1H-indol-3yl)-1,2,3,6-tetrahydro-1-(2H)-pyridin-propanol 71.5 ml of 2 N hydrochloric acid were added to a mixture of the product of Step A in 290 ml of 95% ethanol and the mixture was stirred for 4 hours under an inert atmosphere and then was poured into 500 ml of water. The mixture was made alkaline by addition of sodium hydroxide and was stirred for one hour and filtered. The recovered product was washed with water and dried under reduced pressure to obtain 7.7 g of 4-(5-chloro-1H-indol-3-yl)-1,2,3,6-tetrahydro-1-(2H)-pyridin-propanol in the form of crystals melting at 161.162° C.

A solution of 7.7 g of the said product in 77 ml of ethanol was admixed with a solution of 1.66 g of oxalic acid in 16 ml of ethanol and the mixture was stirred under an inert atmosphere and was vacuum filtered. The product was rinsed with ethanol and was crystallized from distilled water. The mixture was vacuum filtered and the product was rinsed and dried to obtain 7.11 g of neutral oxalate of 4-(5-chloro-1H-indol-3-yl)-1,2,3,6-tetrahydro-1-(2H)-pyridin-pyropanol melting at 195° C. and then 217° C.

Analysis: $C_{34}H_{40}Cl_2N_4O_6$: molecular weight = 671.627

Calculated: %C 60.80; %H 6.00; %Cl 10.55; %N 8.34; Found: %C 60.7; %H 6.0; %Cl 10.8; %N 8.2.

EXAMPLE 8

Tablets were prepared containing either 30 mg of 3-(1-propyl-1,2,3,6-tetrahydro-4-pyridinyl)-5-nitro-1H-indole hydrochloride or 30 mg of the neutral oxalate of 4-(1H-indol-3-yl)-3,6-dihydro-1-(2H)-pyridin-ethanol or 50 mg of 3-(1-propyl-1,2,3,6-tetrahydro-4-pyridinyl)-5-methylthio-1H-indole hydrochloride and sufficient excipient of lactose, starch, talc and magnesium stearate for a final tablet weight of 100 mg.

PHARMACOLOGICAL DATA

A. Antagonism of amphetamine stereotypies

The tests were effected on groups of 5 male rats weighing 150 to 180 g with the animals individually placed in a grilled cage (29×25×17 cm) containing a few scraps of wood chips. A delay of one hour was observed between the intraperitoneal administration of the test compound and the intraperitoneal injection of 8 mg/kg of dexamphetamine sulfate and the behavior of the animals was noted every half hour for 5 hours with the preconceived readings of Halliwell et al. [Brit. J. Pharmacol., Vol. 23 (1964), p. 330-350] as follows: The animal was asleep (0), the animal was awake but immobile, (1), the animal was turning in the cage (2), the animal was sniffing the cover (3), the animal was licking the sides (4), the animal was touching the shavings or bars of the cage with his teeth (5), and the animal was gnawing on the bars or shavings of the cage (6).

The intensity of the stereotypies were expressed in a form of a score of 0 to 30 corresponding to the total of the values obtained for each group of 5 rats. The sum of the scores totaled in 5 hours was calculated. The dose of the test compound which decreased by 50% the sum of the scores in 5 hours was 20 mg/kg for the compound of Example 4 and 25 mg/kg for the compound of Example 2.

B. Antagonism to apomorphine stereotypies

The test was inspired by Janssen et al. [Arzneim. Forsch., Vol. 15 (1965), p. 104-117 and Vol. 17 (1967), p. 841-854] with groups of 5 rats. Each rat was individually placed in a plexiglass box measuring 20×10×10 cm in the bottom of which there was placed a thin layer of wood shaving. A dose of 1.5 mg/kg of apomorphine hydrochloride was intraveinously administered 30 minutes after the intraperitoneal administration of the test compound. The animals were observed for one minute, 15 minutes after the apomorphine injection and the stereotype movements of the oral sphere were evaluated by the Boissier et al. method [Therapie, Vol. 25, (1970), p. 933-949]: (0) characteristic reaction; (1) few sniffles, licking and gnawing (2) intense sniffles and continuous licking and (3) continuous gnawing. The intensity of the stereotypes was expressed as a score of 0 to 15 which was the sum of the values obtained from the 5 rats of a group 15 minutes after the apomorphine injection. The dose which reduced by 50% the scores was 2 mg/kg for the compound of Example 2 and 7 mg/kg for the compound of Example 1.

C. Antagonism towards catalepsy caused by prochloropemazine

The test was effected on groups of 5 male rats weighing about 100 g and the test compound was administered intraperitoneally simultaneously with the intraperitoneal administration of 15 mg/kg of prochlorpemazine. The catalepsy was observed every hour for 7 hours following the test of crossing of homolateral paws [Boissier et al., Therapie, Vol. 18 (1963), p. 1257-1277] with the following notations: The animal refused to cross the front paws with the homolateral rear paws (0); the animals accepted the crossing only for one side (0.5) and the animal accepted the crossing of both sides (1). The compound of Example 1 opposed catalepsy induced by prochlorpemazine at a dose of 10 mg/kg while the compound of Example 5 was effective at a dose of 20 mg/kg. This anti-cataleptic action was particularly interesting as it manifested at low doses than those products exerting themselves a cataleptic effect.

D. Antiemetic Activity

The antagonism to vomitting provoked by apomorphine was studied in dogs [Chen et al., J. Pharmac., exp. Therap., Vol. 93 (1959), p. 245-250] and the number of vomits provoked by subcutaneous injection of 0.1 mg/kg of apomorphine hydrochloride was determined for each animal 8 days before the test. The test compound in aqueous solution was subcutaneously administered at varying doses one half hour before the apomorphine hydrochloride. The compound of Example 2 reduced by 50% the vomits provoked of apomorphine at a dose of 0.01 mg/kg while the compound of Example 1 reduced by 50% the vomits at a dose of 0.08 mg/kg.

E. Acute Toxicity

The acute toxicity was determined on groups of 10 mice weighing about 20 g and the test compounds were intraperitoneally administered at increasing doses. The mortality was determined 48 hours after the administration and the $LD_{50}$ dose for the compounds of Examples 1 and 2 was 200 mg/kg and was 300 and >400 mg/kg, respectively, for the compounds of Examples 5 and 4.

Various modifications of the products and processes of the invention may be made without departing from the spirit or scope thereof and it is to be understood that the invention is intended to be limited only as defined in the appended claims.

We claim:

1. A compound selected from the group consisting of an indole of the formula

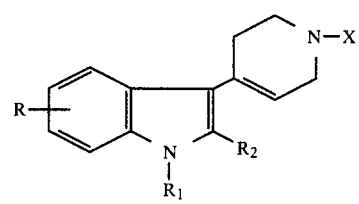

wherein X is selected from the group consisting of alkyl of 1 to 6 carbon atoms, alkenyl of 2 to 5 carbon atoms, alkynyl of 3 to 5 carbon atoms, cycloalkyl of 5 to 6 carbon atoms, cycloalkylalkyl of 4 to 7 carbon atoms, aralkyl of 7 to 12 carbon atoms, hydroxyalkyl of 2 to 5 carbon atoms and phenoxyalkyl of 1 to 5 alkyl carbon atoms, R is selected from the group consisting of hydrogen, halogen, alkoxy of 1 to 3 carbon atoms, nitro, amino, trifluoromethyl and methylthio, $R_1$ and $R_2$ are individually selected from the group consisting of hydrogen and alkyl of 1 to 3 carbon atoms with the proviso that if R is hydrogen, halogen or alkoxy of 1 to 3 carbon atoms, X must be hydroxyalkyl or phenoxyalkyl and their non-toxic, pharmaceutically acceptable acid addition salts.

2. A compound of claim 1 wherein X is hydroxyalkyl of 2 to 5 carbon atoms.

3. A compound of claim 1 wherein X is phenoxyalkyl of 1 to 5 alkyl carbon atoms.

4. A compound of claim 1 wherein X is alkyl of 1 to 6 carbon atoms, cycloalkyl of 5 to 6 carbon atoms, cycloalkylalkyl of 4 to 7 carbon atoms, alkenyl of 2 to 5 carbon atoms, alkynyl of 3 to 5 carbon atoms or aralkyl of 7 to 12 carbon toms when R is —$NO_2$, —$NH_2$, —$CF_3$ or $CH_3S$—.

5. A compound of claim 4 which is 3-(1-propyl-1,2,3,6-tetrahydro-4-pyridinyl)-5-nitro-1H-indole hydrochloride.

6. A antipsychotic composition comprising an antipsychotically effective amount of at least one compound of claim 1 and an inert pharmaceutical carrier.

7. A composition of claim 6 wherein X is hydroxyalkyl of 2 to 5 carbon atoms.

8. A composition of claim 6 wherein X is phenoxyalkyl of 1 to 5 alkyl carbon atoms.

9. A composition of claim 6 wherein X is alkyl of 1 to 6 carbon atoms, cycloalkyl of 5 to 6 carbon atoms, cycloalkylalkyl of 4 to 7 carbon atoms, alkenyl of 2 to 5 carbon atoms, alkynyl of 3 to 5 carbon atoms or aralkyl of 7 to 12 carbon atoms and R is —$NO_2$, —$NH_2$, —$CF_3$ or $CH_3S$—.

10. A composition of claim 6 wherein the active compound is 3-(1-propyl-1,2,3,6-tetrahydro-4-pyridinyl)-5-nitro-1H-indole hydrochloride.

11. A method of inducing antipsychotic activity in a warm-blooded animal comprising administering to a warm-blooded animal an amount of at least one compound of claim 1 sufficient to induce antipsychotic activity.

12. A method of claim 11 wherein X is hydroxyalkyl of 2 to 5 carbon atoms.

13. A method of claim 11 wherein X is phenoxyalkyl of 1 to 5 alkyl carbon atoms.

14. A method of claim 11 wherein X is alkyl of 1 to 6 carbon atoms, cycloalkyl of 5 to 6 carbon atoms, cycloalkylalkyl of 4 to 7 carbon atoms, alkenyl of 2 to 5 carbon atoms, alkynyl of 3 to 5 carbon atoms or aralkyl of 7 to 12 carbon atoms when R is —$NO_2$, —$NH_2$, —$CF_3$ or $CH_3S$—.

15. The method of claim 11 wherein the active compound is 3-(1-propyl-1,2,3,6-tetrahydro-4-pyridinyl)-5-nitro-1H-indole hydrochloride.

* * * * *